United States Patent [19]

Scriven et al.

[11] Patent Number: 5,446,163

[45] Date of Patent: Aug. 29, 1995

[54] PREPARATION OF HYDRAZONES, DIHYDROTHIADIAZOLES AND TRIAZINONES

[75] Inventors: Eric F. V. Scriven, Greenwood; James G. Keay; Tony Zhang, both of Indianapolis, all of Ind.

[73] Assignee: Reilly Industries, Inc., Indianapolis, Ind.

[21] Appl. No.: 955,691

[22] Filed: Oct. 2, 1992

[51] Int. Cl.⁶ .......................................... C07D 417/04
[52] U.S. Cl. ................................ 546/277; 544/182; 546/268; 546/280; 546/332
[58] Field of Search ................ 544/182; 546/268, 277, 546/280, 332

[56] References Cited

U.S. PATENT DOCUMENTS

| | | | |
|---|---|---|---|
| 4,237,275 | 12/1980 | Bader et al. | 546/314 |
| 4,322,536 | 3/1982 | Bader et al. | 546/314 |
| 4,489,073 | 12/1984 | Hargreaves et al. | 544/8 |
| 4,489,074 | 12/1984 | Brown et al. | 544/8 |
| 4,495,185 | 1/1985 | Brown et al. | 544/182 |
| 4,558,045 | 12/1985 | Hargreaves et al. | 514/222 |
| 4,584,298 | 4/1986 | Brown et al. | 514/242 |
| 4,694,005 | 9/1987 | Brown et al. | 514/234 |
| 4,699,913 | 10/1987 | Farooq et al. | 514/333 |
| 4,716,164 | 12/1987 | Hargreaves et al. | 514/242 |
| 4,788,194 | 11/1988 | Hargreaves et al. | 544/182 |
| 4,812,464 | 3/1989 | Farooq et al. | 514/333 |
| 4,853,396 | 8/1989 | Farooq | 546/256 |
| 4,870,184 | 9/1989 | Farooq et al. | 546/264 |
| 4,897,485 | 1/1990 | Farooq | 546/264 |
| 4,931,439 | 6/1990 | Kristinsson | 544/182 |
| 4,996,325 | 2/1991 | Kristinsson | 548/132 |

FOREIGN PATENT DOCUMENTS 9202507 8/1991 WIPO.

OTHER PUBLICATIONS

Farooq et al., "The Phototransformation of a Bis-2,-3-diazabutadienyldisulfide to a Aphicidally Active 2,3-Dihydro-1,3,4-thiadiazole", *Pestic. Sci.*, vol. 30, pp. 199-209 (1990).

*Primary Examiner*—Yogendra N. Gupta
*Attorney, Agent, or Firm*—Woodard, Emhardt, Naughton Moriarty & McNett

[57] ABSTRACT

Processes for preparing pyridyl-substituted hydrazoles, dihydrothiadiazones or aminotriazinones by reaction of iminopyridines preformed in situ or otherwise with hydrazides or carbazides, or their sulfur counterparts, or with aminotriazinones.

10 Claims, No Drawings

PREPARATION OF HYDRAZONES, DIHYDROTHIADIAZOLES AND TRIAZINONES

BACKGROUND

The present invention resides generally in the field of preparative methods for pyridylhydrazones, pyridyldihydrothiadiazoles, and N-pyridylmethylene aminotriazinones.

Certain of these pyridylhydrazones, pyridyldihydrothiadiazoles and N-pyridylmethylene aminotriazinones have been the subject of significant research for their commercial utility as pesticidal compounds and intermediates to pesticidal compounds. This research is exemplified in U.S. Pat. Nos. 4,699,912; 4,812,464; 4,870,184; 4,853,396; 4,897,485; 4,931,439 and 4,996,325. These compounds have been synthesized, invariably, by condensing pyridinecarboxaldehyde with a hydrazide, thiohydrazide or aminotriazinone. This route, however, is disadvantageous because the pyridinecarboxaldehyde starting materials are potent skin sensitizers and are also unstable, expensive and difficult to prepare.

What is therefore needed is an efficient route to these pyridyl-substituted hydrazones, dihydrothiadiazoles and triazinones that avoids or minimizes the nature of the use of these unstable, noxious pyridinecarboxaldehyde starting materials. The present invention addresses this need.

SUMMARY OF THE INVENTION

One preferred embodiment of the invention relates to a process for preparing a pyridyl-substituted hydrazone, dihydrothiadiazole or triazinone compound, which comprises a condensation reaction of an iminomethylpyridine of the formula Py—CH=N—R, wherein Py is a 2-, 3- or 4-pyridyl radical and R is alkyl, aryl, or aralkyl, with a compound of the formula I:

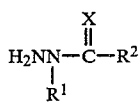

wherein when X is O or S, $R^2$ is substituted or unsubstituted alkyl, aryl or heteroaryl, and $R^1$ is H; or when X is O, then $R^1$—N—CX—$R^2$ in formula I, taken together, may form a cyclic group of the formula

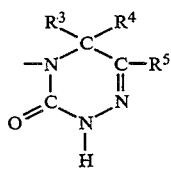

wherein $R^3$ is H or substituted or unsubstituted alkyl, alkoxy, aryl, or aralkyl (i.e. -alkyl-aryl); $R^4$ is H or substituted or unsubstituted alkyl, cycloalkyl or aryl; or $R^3$ and $R^4$ together may form a saturated or unsaturated carbocycle; and $R^5$ is H or substituted or unsubstituted alkyl, cycloalkyl, alkoxy, aryl, or aralkyl; to form a compound of the formula II when X is O and a compound of the formula III when X is S:

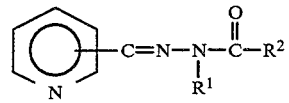

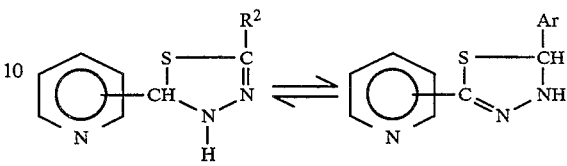

wherein $R^1$ and $R^2$ are as defined above.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

The present invention relates to a condensation reaction between an iminomethylpyridine and a hydrazide or a carbazide, or their sulfur counterparts, or an aminotriazinone. The reaction acts to eliminate a molecule of primary amine and form a pyridyl-substituted hydrazone, dihydrothiadiazole or aminotriazinone compound in the process.

The iminomethylpyridine used in the invention may be a 2-, 3- or 4-iminopyridine, having the general formula Py—CH=N—R, wherein Py is the 2-, 3- or 4-pyridyl radical and R is alkyl, aryl or aralkyl. In this regard, the alkyl, aryl or aralkyl group can be substituted or unsubstituted. When substituted, the substituents will be groups that do not detrimentally interfere with the condensation reaction as will be known or readily ascertainable by those ordinarily skilled in this field. Branched or unbranched lower alkyl groups, for example $C_1$ to $C_5$, branched or unbranced alkyl groups, e.g., containing methyl, ethyl, n-propyl, isopropyl, n-butyl, isobutyl, n-pentyl, isopentyl, are preferred for R from work done thus far. This is especially true for those which provide an elimination condensation product of the formula $RNH_2$, which can be readily removed by evaporation.

The iminomethylpyridine starting material can be obtained using techniques known to the art and literature. For example, the corresponding pyridinecarboxaldehyde can be reacted with an amine of the formula $H_2N$—R to thereby produce the iminopyridine having the formula, Py—CH=N—R, wherein Py and R are as defined above. Iminomethylpyridines are also available via direct hydrogenation of cyanopyridines in situ in the presence of amines with various attendant advantages, as described in Publication No. WO 92/02507, Feb. 20, 1992 (publishing PCT Application No. PCT/US91/05604, Reilly Industries, Inc.) which is hereby incorporated by reference in its entirety. Still further methods which are or may become known to the art may be used herein, and are within the contemplation and scope of this invention. In any case, starting the underlying condensation reaction with this iminomethylpyridine material already formed in situ or otherwise is in a marked advance over prior such reactions in view of its improved stability and storage characteristics as well as its improved efficiency and ease of handling and use as compared to the prior art use of pyridinecarboxaldehydes.

This iminomethylpyridine starting material is then caused to undergo a condensation reaction with a reactant selected from a hydrazide or a carbazide, or their sulfur equivalents, or an aminotriazinone. This reactant compound will have the general formula I:

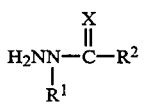

wherein when X is O or S, $R^2$ is substituted or unsubstituted alkyl, aryl or heteroaryl, and $R^1$ is H; or when X is O, $R^1$—N—CX—$R^2$ in formula I, taken together, may form a cyclic group of the formula

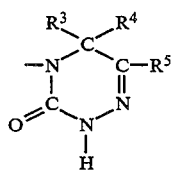

wherein $R^3$ is H or substituted or unsubstituted alkyl, alkoxy, aryl, or aralkyl (i.e., -alkyl-aryl); $R^4$ is H or substituted or unsubstituted alkyl, cycloalkyl or aryl; or $R^3$ and $R^4$ together may form a saturated or unsaturated carbocycle; and $R^5$ is H or substituted or unsubstituted alkyl, cycloalkyl, alkoxy, aryl, or aralkyl.

Compounds of the formula I above, and their preparations, are generally known in the art. For example, reference can be made to those specific compounds described in U.S. Pat. Nos. 4,699,912; 4,812,464; 4,870,184; 4,853,396; 4,897,485; 4,931,439 and 4,996,325.

The condensation reaction that takes place between the iminomethylpyridine material and the reactant compound of formula I above produces a hydrazone or triazinone compound of the formula II below when X is O, or produces a dihydrothiadiazole compound of the formula III below when X is S:

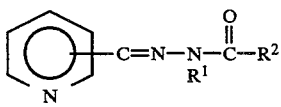

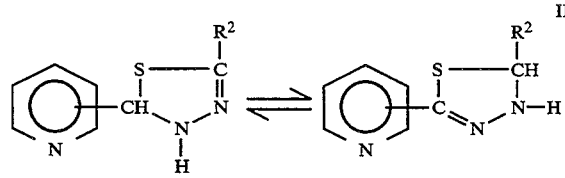

In these formulas, $R^1$ and $R^2$ are as defined above in connection with formula I.

Relating to these compounds and formulas, where a radical group is described herein as being substituted, the substituent or substituents will be typical to the art to which the invention pertains. Numerous such substituents are known, and are described for instance in the various U.S. patents cited herein. These substituents include $C_1$-$C_4$ alkyl, $C_1$-$C_4$ alkoxy, $C_1$-$C_4$ alkylthio, $C_1$-$C_4$ haloalkyl having from 1 to 9 halogen atoms, $C_1$-$C_4$ haloalkoxy having from 1 to 9 halogen atoms, $C_1$-$C_4$ haloalkylthio having from 1 to 9 halogen atoms, aralkyl (i.e., alkyl-aryl, e.g., benzyl), substituted aralkyl, aryloxy, (e.g., phenoxy), substituted aryloxy, arylthio (e.g., phenylthio), substituted arylthio, heteroaryloxy (e.g., pyridyloxy), substituted heteroaryloxy, halogen (e.g., chlorine, bromine, iodine or fluorine), nitro, cyano, and the like.

Preferred products which can be and have been prepared thus far by the preferred process of applicants' invention have the general formula IV:

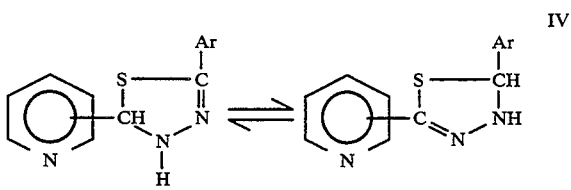

wherein Ar is substituted or unsubstituted aryl, and especially substituted or unsubstituted phenyl. When substituted, the phenyl can have from 1 to 5 substituents, desirably selected from the group consisting of $C_1$-$C_4$ alkyl, $C_1$-$C_4$ alkoxy, $C_1$-$C_4$ alkylthio, $C_1$-$C_4$ haloalkyl having from 1 to 9 halogen atoms, $C_1$-$C_4$ haloalkoxy having from 1 to 9 halogen atoms, $C_1$-$C_4$ haloalkylthio having from 1 to 9 halogen atoms, halogen (e.g. chlorine, bromine, iodine or fluorine), nitro, and cyano. Further preferred products are those wherein Ar is mono- or di-substituted phenyl, especially with the substituent(s) being selected from the group consisting of halogen $C_1$-$C_4$ alkyl trifluoromethyl $C_1$-$C_4$ alkoxy, and nitro. Of special interest are products wherein Ar is a 2- or 4-halophenyl, especially 2- or 4-(chloro or bromo)phenyl. Also preferred are products wherein the pyridinyl radical is a 3-pyridinyl radical.

Additional preferred products which can be and have been prepared in accordance with the invention are N-amino-1,2,4-triazinones of the formula V:

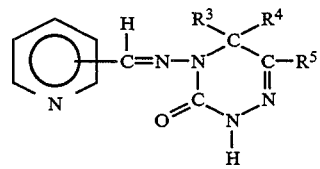

wherein $R^3$, $R^4$ and $R^5$ are as defined above. More preferably, $R^3$ is hydrogen or $C_1$-$C_6$ alkyl; $R^4$ is hydrogen, $C_1$-$C_6$ alkyl or $C_3$-$C_6$ cycloalkyl, or is phenyl that is unsubstituted or substituted by $C_1$-$C_{12}$ alkyl, halogen or by $C_1$-$C_{12}$ haloalkyl; or $R^3$ and $R^4$ taken together form a saturated or unsaturated 3 to 7 membered carbocycle; and $R^5$ is hydrogen, $C_1$-$C_{12}$ alkyl, $C_3$-$C_6$ cycloalkyl, $C_1$-$C_4$ alkoxy-$C_1$-$C_6$alkyl, $C_1$-$C_2$ haloalkyl, phenyl, benzyl, phenethyl, phenpropyl, phenbutyl or phenpentyl radical that is mono- or di-substituted by halogen, $C_1$-$C_5$ alkyl, $C_1$-$C_2$ haloalkyl, methoxy and/or by ethoxy.

These triazinones of formula V can be prepared generally by applicants' above-described condensation reaction. They can also, in particular, be prepared by the condensation reaction of the above 2-, 3- or 4-iminomethylpyridine, Py—CH=N—R, with an aminotriazinone of the formula VI:

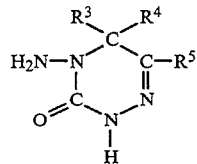

wherein $R^3$, $R^4$ and $R^5$ are as defined above. In this regard, the N-amino-1,2,4-triazinone products of formula V and the aminotriazinone starting materials of formula VI, and their preparation, are known in the art and are further described, for example, in U.S. Pat. No. 4,996,325.

Referring now generally to these above condensation reactions, they can be carried out either neat or, more preferably, in a suitable solvent. Such solvents suitable for this purpose include one or a combination of the following: aromatic hydrocarbons, especially $C_{6-9}$ aromatic hydrocarbons; chlorinated aromatic or aliphatic solvents, e.g., $C_{1-6}$ chlorinated aromatic or aliphatic hydrocarbons; alcohols, especially $C_{1-6}$ alcohols; carboxylic acids and corresponding esters, e.g., acetic acid and its $C_{1-4}$ alkyl esters; and the like. Preferred solvents from work done thus far are lower alcohols, e.g., $C_1$–$C_4$ alcohols.

The preferred condensation reactions above can be carried out at any suitable temperature that leads to the formation of the desired product. Such temperatures are known to or readily ascertainable by those of ordinary skill in this area. Typically, these temperatures will be in the range of about $-15°$ C. to about $100°$ C. As this range suggests, conveniently, these preferred condensation reactions can be successfully conducted at ambient temperatures.

As one alternative, catalysts such as protonic or Lewis acids are or may be beneficial to the reaction, but are not necessary. Thus, to date preferred processes for applicants' invention are and have been conducted using catalysts such as a suitable Lewis acid, and preferably an organic acid such as acetic acid.

The products produced by these preferred processes can be and have been conventionally employed as pesticidal compounds or as intermediates to pesticidal compounds. As pesticides, they may be used in unmodified form, but are typically used together with adjuvants conventionally employed in such pesticidal formulations. These formulations may take the form of emulsifiable concentrates, solutions which can be sprayed or diluted and then sprayed, dilute emulsions, wettable powders, soluble powders, dusts, granulations, and encapsulations. The pesticide products may also be used together with other pesticides. These and other facets of pesticide use are well known to the ordinarily skilled artisan in that field.

In order to promote a further understanding of the invention and its preferred embodiments and advantages, the following specific examples are provided. It will be understood, however, that these examples are illustrative and not limiting of the invention. In these examples, common abbreviations known to the art are used. Thus, degrees are given in degrees Celsius (°C.) unless otherwise indicated; "g"= grams; "l"=liters; "mL"=milliliters; mm=millimeters; mp=melting point; mmol=millimoles; ppm=parts per million; GC-MS=gas chromatography-mass spectroscopy; NMR=nuclear magnetic resonance; percent yields are given as percent of theoretical. Similarly, reference has been made to several issued U.S. patents and publications in the written specification herein. The same are hereby incorporated herein by reference in total as to all essential and nonessential subject matter contained therein for the purposes of indicating background of the invention or illustrating the state of the art as well as providing adequate disclosure and supporting the claims herein and describing the nature and scope of applicants' invention.

EXAMPLE 1

3-[5-(4-chlorophenyl)-4,5-dihydro-1,3,4-thiadiazol-2-yl]Pyridine, and

3-[5-(4-chlorophenyl)-2,3-dihydro-1,2,3-thiadiazol-2-yl]Pyridine

A solution of 4-chlorobenzoic thiohydrazide (5 mmol, 0.932 g) in 10 mL of ethanol was stirred with 0.81 g (5 mmol) of 3-(N-butyliminomethyl)pyridine for 1 hour at room temperature. The solution was concentrated in vacuo. 0.97 g of white crystal was obtained by recrystallization from a toluene/hexane (7:2) mixture. mp 147° C.–151° C. (decomposed). GC-MS M+/e 275.

EXAMPLE 2

3-(5-phenyl-4,5-dihydro-1,3,4-thiadiazol-2-yl) pyridine, and 3-(5-phenyl-2,3-dihydro-1,3,4-thiadiazol-2-yl)pyridine These compounds were prepared in a manner similar to that described in the first example, from benzoic thiohydrazide and 3-(N-butyliminomethyl)pyridine in 75% yield.

EXAMPLE 3

N-(3-pyridinylmethylene) benzoic hydrazide

To a mixture of benzoic hydrazide (2.72 g, 20 mmol) in 40 mL of EtOH were added 3.24 g (20 mmol) of N-butyliminomethylpyridine. The resulting solution was stirred for 1 hour at room temperature. The white precipitate was filtered and dried to give 4.43 g (98%) of the title compound.

EXAMPLE 4

Benzoic thiohydrazide

The literature procedure (CA 50:8730 g) was followed. To a solution of carbon disulfide (22.8 mL) in 100 mL of THF was added PhMgBr (2M in diethyl ether, 200 mL, 400 mmol) dropwise. The reaction temperature was controlled below 45° C. so as to maintain a gentle reflux of $CS_2$. The resulting deep red mixture was stirred for 1 hour, cooled to ambient temperature, poured onto 150 g of ice, acidified with 2N HCl to pH 0.5, and extracted with $CH_2Cl_2$ until the aqueous phase became colorless (4×40 mL). The methylene chloride extract was then stirred with 100 mL of 50% aqueous hydrazine for 5 minutes. The aqueous layer was taken out, while the organic layer was subjected to the same hydrazine treatment again. The combined hydrazine layer was acidified with cooling to pH 5.6 with approximately 90 mL of glacial acetic acid. The solution was extracted first with 2×100 mL of toluene, and then 3×100 mL of $CH_2Cl_2$. The combined organic phases were dried over MgSO₄, concentrated to afford a yellow powder which was recrystallized from MeOH-Hexane to give 21 g of yellow needle-shaped crystal (35%, mp 76°–81° C., uncorrected). $^1$H NMR ($\delta$) 7.1–7.8(m, 5H), 5.9–6.3 (bs, 3H).

EXAMPLE 5

4-Chlorothiobenzoylmorpholine

This compound was prepared according to the procedure described by U.S. Pat. No. 4,694,005. A mixture of 4-chlorobenzaldehyde (42.15 g, 300 mmol), sulfur powder (12 g, 375 mmol), and morpholine (120 g) was refluxed for 1 hour. The resulting mixture was poured onto water, stirred, filtered, and washed with water. The yellow solid was then dissolved in 1l of hot methanol and filtered while hot. The filtrate was allowed to stand at room temperature overnight to give 38.2 of yellow needle-shaped crystal which contained one molecule of MeOH as indicated by $^1$H NMR. (48%, mp. 128° C.–131° C.) $^1$H NMR ($\delta$) 3.5 (s, 3 H), 3.7–4.0 (m, 4 H), 4.2–4.5 (m, 4 H), 7.1–7.3 (bs, 4 H).

EXAMPLE 6

4-Chlorobenzoic thiohydrazide

This compound was prepared by a modification of the literature procedure (U.S. Pat. No. 4,558,045). 4-Chlorothiobenzoylmorpholine (12.17 g, 50 mmol) was added to 100 mL of anhydrous hydrazine at room temperature and stirred for 2 hours, while most solid dissolved. The foamy material formed in the process was filtered off and the filtrate was carefully neutralized with glacial acetic acid with cooling by means of an ice bath. The solution was extracted with diethyl ether ($4\times100$ mL), washed with water ($2\times50$ mL), dried over MgSO₄ and concentrated. The resulting yellow residue was recrystallized several times from CH₂Cl₂ to afford 4 g (43%) of the title compound in the form of yellowish crystals. (mp 125°–127° C.). $^1$H NMR ($\delta$) 7.2 (2 H, d, J=10 Hz), 7.6 (2 H, d, J=10 Hz) ppm.

EXAMPLE 7

Hydrazones

The corresponding pyridylhydrazones of formula II are obtained by practicing the preferred condensation reaction as above-described. In particular, 3-butyliminopyridine is reacted at a suitable temperature with a reactant of the formula I wherein X is O and R₂ is It in each case, and wherein R¹ is selected from the group consisting of phenyl, 4-chlorophenyl, 4-methoxyphenyl, 4-methylphenyl, 4-trifluormethylphenyl, 4-cyanophenyl, 4-trifluoromethoxyphenyl, 2-chlorophenyl, 3-chlorophenyl, 3-nitrophenyl, and 2,4-dichlorophenyl. The resultant product is then recovered following the reaction, and used in connection with its known pesticidal properties.

EXAMPLE 8

Pyridyltriazinones

The corresponding pyridyltriazinones of formula V are obtained by conducting the preferred condensation reaction as above-described using 3-butyliminopyridine as a starting material. The reactant compound used was of the formula VI, in which R³, R⁴ and R⁵ are as defined in the following table:

| Reactant Constituents | | |
|---|---|---|
| R³ | R⁴ | R⁵ |
| H | H | H |
| CH₃ | CH₃ | CH₃ |
| C₂H₅ | C₂H₅ | C₂H₅ |
| CH₃CH₂CH₂ | CH₃CH₂CH₂ | phenyl |
| CH₃ | H | cyclopropyl |
| H | H | 4-chlorophenyl |
| H | CH₃ | phenylmethyl |
| CH₃ | H | phenylpropyl |
| CH₃ | CH₃ | phenylpropyl |

EXAMPLES 9

Pyridyldihydrothiadiazoles

Various preferred pyridyldihydrothiadiazoles of the formula III above are obtained by condensation reaction as also above-described. The starting material employed is 3-butyliminopyridine and the reactant of formula I is used, wherein X is S and R¹ is H in each case, and where R² is selected from the group consisting of phenyl, 4-chlorophenyl, 4-methoxyphenyl, 4-methylphenyl, 4-trifluormethylphenyl, 4-cyanophenyl, 4-trifluoromethoxyphenyl, 2-chlorophenyl, 3-chlorophenyl and 3-nitrophenyl. The products of the reaction exhibit valuable pesticidal properties as known in the art.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A process for preparing a pyridyl-substituted dehydrothiadiazole compound, which comprises a condensation reaction of an iminomethylpyridine of the formula Py—CH=N—R wherein Py is a 2-, 3- or 4-pyridyl radical and R is alkyl, aryl, or aralkyl, with a compound of the formula:

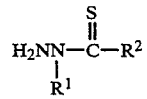

wherein R¹ is H, and R² is phenyl which is unsubstituted or is substituted with one or more substituents selected from the group consisting of C₁–C₄ alkyl, C₁–C₄ alkoxy, C₁–C₄ aklylthio, C₁–C₄ haloalkyl having from 1 to 9 halogen atoms, C₁–C₄ haloalkylthio having from 1 to 9 halogen atoms, halogen, nitro, and cyano, so as to form a compound of the formula:

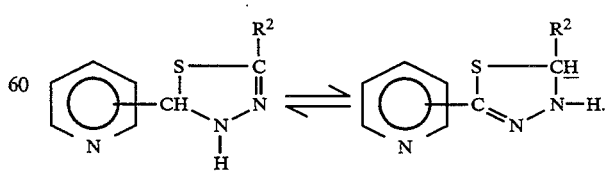

2. The process of claim 1 wherein R² is an unsubstituted phenyl group.

3. The process of claim 1 wherein R² is a halogen-substituted phenyl group.

4. The process of claim 3 wherein $R^2$ is a chloro-substituted phenyl group.

5. The process of claim 4 wherein $R^2$ is 4-chlorophenyl.

6. The process of claim 1 wherein the reaction is conducted in a solvent.

7. The process of claim 6 wherein the solvent is an alcohol.

8. The process of claim 7 wherein the solvent is a $C_1$ to $C_4$ alcohol.

9. The process of claim 6 wherein the reaction is conducted in the presence of a catalytic amount of a protonic or Lewis acid catalyst.

10. The process of claim 8 wherein the reaction is conducted in the presence of a catalytic amount of a protonic or Lewis acid catalyst.

* * * * *

UNITED STATES PATENT AND TRADEMARK OFFICE
CERTIFICATE OF CORRECTION

PATENT NO. : 5,446,163            Page 1 of 2

DATED : August 29, 1995

INVENTOR(S) : Eric F.V. Scriven et al

It is certified that error appears in the above-indentified patent and that said Letters Patent is hereby corrected as shown below:

In column 2, please replace the figure: 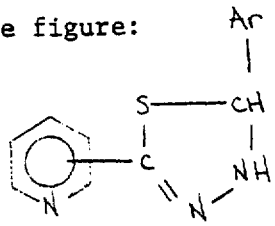

with the figure

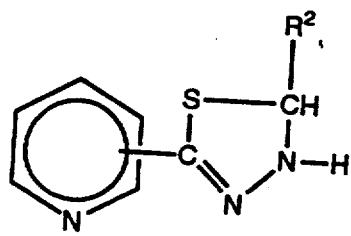

UNITED STATES PATENT AND TRADEMARK OFFICE
CERTIFICATE OF CORRECTION

PATENT NO. : 5,446,163                              Page 2 of 2
DATED      : August 29, 1995
INVENTOR(S) : Eric F.V. Scriven et al It is certified that error appears in the above-indentified patent and that said Letters Patent is hereby corrected as shown below:

In column 7, line 51, please delete "It" and insert in lieu thereof --H--.

Signed and Sealed this

Twenty-eighth Day of November 1995

Attest:

BRUCE LEHMAN

Attesting Officer      Commissioner of Patents and Trademarks